United States Patent [19]

Worrell et al.

[11] Patent Number: 5,112,456

[45] Date of Patent: May 12, 1992

[54] ELECTROCHEMICAL SENSORS AND METHODS FOR THEIR USE

[75] Inventors: Wayne Worrell, Narberth, Pa.; Qingguo Liu; Yuhua Tang, both of Bejing, China

[73] Assignee: Trustees of the University of Pennsylvania, Philadephia, Pa.

[21] Appl. No.: 449,781

[22] Filed: Dec. 12, 1989

[51] Int. Cl.⁵ .......................................... G01N 27/411
[52] U.S. Cl. ................................ 204/153.18; 204/422
[58] Field of Search .................. 204/422, 423, 153.18, 204/421, 424

[56] References Cited

U.S. PATENT DOCUMENTS

| | | | |
|---|---|---|---|
| 3,772,177 | 11/1973 | Rittiger et al | 204/422 |
| 3,773,641 | 11/1973 | Fitterer | 204/423 |
| 3,809,639 | 5/1974 | Faurschou et al. | 204/423 |
| 4,045,300 | 8/1977 | Renet | 204/422 X |
| 4,045,319 | 8/1977 | Deportes et al. | 204/424 |
| 4,141,812 | 2/1979 | Kawawa et al. | 204/422 |
| 4,166,019 | 8/1979 | Roy et al. | 204/422 |
| 4,193,857 | 3/1980 | Bannister et al. | 204/153.18 X |
| 4,328,294 | 5/1982 | Tanaka et al. | 204/424 |
| 4,428,770 | 1/1984 | Worrell et al. | 75/384 |
| 4,627,892 | 12/1986 | Worrell et al. | 204/153.18 |
| 4,632,732 | 12/1986 | Fog et al. | 204/416 X |
| 4,695,361 | 9/1987 | Grady | 204/415 |
| 4,786,374 | 11/1988 | Worrell et al. | 204/153.18 |

OTHER PUBLICATIONS

"Developing New Electrochemical Sensors", Proceedings of the Symposium on Metal-Slag-Gas Reactions & Processes, Electrochemical Society, Princeton, N.J., (May 1975).
Oxide Solid Electrolytes, Worrell.
New Zirconia-Electrolyte Sensors for Measuring in Iron and Steel Melts, Proceedings of the Symposium on Chemical Sensors, D. R. Turner, ed, Electrochemical Society, vol. 87-9 (1987).
The Measurement of Oxygen Chemical Potentials for the Calcium Fluoride Solid Electrolyte, Worrell et al., Journal of the Electrochemical Society, vol. 126, No. 8, pp. 1360-1363 (1979).
The Measurement of Sulfur Chem. Potential Diff. Using a Calcium Fluoride Solid Elec., Worrell et al., Journal of the Electrochemical Society, vol. 127, pp. 1717-1721, Aug. 1980.
Galvanic-Cell Investigation with a $CaF_2$ Solid Electrolyte at Elevated Temperatures, Worrell, Solid State Ionics, vol. 3/4, pp. 559-563 (1981).
Development of the High-Temperature Technology, JUPAC, pp. 503-509 (1969).
Janke Solid State Ionics, vol. 3/4, pp. 559-604 (1981).

*Primary Examiner*—T. Tung
*Attorney, Agent, or Firm*—Woodcock Washburn Kurtz Mackiewicz & Norris

[57] ABSTRACT

Electrochemical sensors are provided having improved sensitivity, stability and dirability. In accordance with preferred embodiments, such sensors comprise protective sheath means having at least one opening. Within the sheath and sealed thereto at the opening is a sensing body comprising metal oxide and an oxide from group IIA or IIB of the periodic table. Reference electrode means are also provided. Methods for monitoring the concentration of a species in a melt are also provided.

19 Claims, 2 Drawing Sheets

*Fig. 4*

ELECTROCHEMICAL SENSORS AND METHODS FOR THEIR USE

BACKGROUND OF THE INVENTION

This invention is directed to electrochemical sensors having improved sensitivity, stability and durability. This invention is also directed to methods for employment of such sensors, especially for the determination of oxygen concentrations in melts. Such, improved sensors are far more durable than prior sensors and are generally easy to manufacture. Sensors in accordance with the present invention are capable of long-term use, especially as oxygen sensors in steel and other melts.

The present invention is also suitable for the preparation of electrochemical sensors for molecular or atomic species other than oxygen. Thus, sulfur, carbon, and other electrochemically sensible species may be detected at high temperatures in corrosive environments and in metallurgical and other melts in accordance with the practice of one or more embodiments of the present invention.

The detection of elemental and molecular species is an important aspect of numerous industrial and other procedures. For example, the detection of oxygen, sulfur, carbon and other species in metallurgical melts, in flue gasses in chemical reactors and in other high temperature or corrosive situations is critical to the metals, utilities, chemicals, vitreous products and other industries. Moreover, caustic, corrosive, oxidative and other harsh conditions and environments strain the ability of sensor manufacturers to prepare electrochemical sensing devices capable of surviving such conditions and environments while retaining the ability to perform the desired sensing duties in an accurate and reliable fashion and for reasonable periods of time.

One area presenting particularly stringent requirements for sensing devices is the field of metals purification and processing. It is commonly necessary to measure the oxygen, sulfur, carbon and other contents of molten metals such as iron and steel. To do so, it is known to immerse electrochemical sensors in such melts. The electromotive force, EMF, generated by the sensor is then monitored and related to the activity or concentration of the atomic or molecular species of interest. Heretofore, many electrochemical sensors for the testing of such melts have demonstrated severe shortcomings including short operating lifetimes (often only a few minutes), high failure rates, poor reproducibility, low sensitivity and other faults.

General considerations for the development of electrochemical sensors, especially those useful in metallurgical melts, are discussed in Worrell, "Developing New Electrochemical Sensors", Proceedings of the Symposium on Metal-Slag-Gas Reactions and Processes, Electrochemical Society, Princeton, N.J., (May 1975), incorporated herein by reference. Thus, it has long been desired to provide electrochemical sensors, especially those suitable for harsh environments, which exhibit improved sensitivity, long-term physical and electrochemical stability, and physical durability.

It has also long been desired to provide methods for the preparation of electrochemical sensors which are, at once, effective in obtaining improved sensor qualities while securing reduced manufacturing costs. Methods of sensing and measurement which provide more accurate, longer term, and more sensitive information have also been sought. Prior to the present invention, however, these long felt needs have not been satisfied. Improvements attempted by others have failed to attain the desired goals.

Electrochemical sensors adapted for the measurement of oxygen in liquids such as in metallurgical metals are known. See in this regard "Developing New Electrochemical Sensors", Worrell, supra; "Oxide Solid Electrolytes", Worrell, Topics in Applied Physics, Geller Ed., Springer (1977); and "The Measurement of Oxygen Chemical Potentials for the Calcium Fluoride Solid Electrolyte", 'Worrell et al., Journal of the Electrochemical Society, Vol. 126, No. 8, pp. 1360-1363 (1979). The foregoing references are incorporated herein by reference in order to describe more fully the electrochemical determination of elemental compositions employing solid electrolyte sensors. The foregoing publications disclose the employment of certain simple solid solutions as those of zirconium oxide and thorium oxide in the electrochemical detection of oxygen.

Electrolytes suitable for the electrochemical measurement of sulfur or carbon under laboratory conditions have been disclosed. Calcium fluoride, for example, has been proposed for such use. See "The Measurement of Sulfur Chemical Potential Differences Using a Calcium Fluoride Solid Electrolyte," Worrell et al., Journal of the Electrochemical Society. *Electrochemical Science and Technology*, vol 127, pp. 1717-1721, August 1980; and "Galvanic-Cell Investigation With a $CaF_2$ Solid Electrolyte at Elevated Temperatures," Worrell, Solid State Ionics vol. ?, pp. 559-563 (1981). Further attempts at the electrochemical measurement of sulfur have been reported. Thus, the employment of calcium sulfide-based electrolytes is reported in "Development of the High-Temperature Technology, JUPAC, pp. 503-509 (1969). In U.S. Pat. No. 4,428,770, Worrell et al., novel sulfur and carbon sensors for metallurgical applications are disclosed. That patent together with each of the foregoing references are incorporated herein by reference. Other systems for measuring sulfur and carbon potentials are discussed therein.

For many years, oxygen sensors for metallurgical melts have been constructed from zirconia, $ZrO_2$, partially stabilized with aliovalent materials such as calcium oxide, CaO or magnesia, MgO. Thus, in one type of sensor a calcium oxide-stabilized zirconia solid electrolyte pellet was welded into a quartz tube for insertion into melts. The tube was either open to a gas (such as the atmosphere) to provide a source of reference potential, or was provided with a solid reference electrode material such as a metal-metal oxide mixture. EMF measurement and thermocouple means were also typically provided as appropriate. Such electrochemical sensors, while capable of some uses in metal melts, suffered from a lack of physical integrity leading to unreliable data, lack of reproducibility, and failure after short periods of time when placed into metallurgical service.

In the 1970's, efforts were made to develop improved solid electrolyte-based sensors, especially oxygen sensors, for metal melts. In this regard, it was hoped to overcome the physical instability and tendency toward thermal fracture of previous sensors through stabilization of the electrochemical material and improved physical processing methods for the sensor fabrication. The quartz tube was discarded and a tube formed from the electrolyte material itself employed. Partially stabilized zirconia, $ZrO_2$ with about 3 wt% of MgO, was blended together, formed into a tubular shape, compacted, and densified through sintering. The resulting, sintered electrolyte material comprised three phases, cubic, tetragonal, and monoclinic and exhibits improved mechanical strengths and resistance to thermal shock. The tube can be filled with a solid reference electrode material together with thermocouple and electrical lead means as desired.

The tube comprising a three-phase electrolyte can be used as an oxygen sensor in metallurgical melts and is widely used for this purpose today. While exhibiting utility for this purpose, the foregoing electrolyte--tube devices still suffer from severe shortcomings. Such devices are extremely short-lived, being capable of use on the order of only a few minutes. While after special modification some tubes can last for as long as ten minutes before usefulness is lost, such lifetime is far less than is desired and the resulting data is of poor quality. Since the partially stabilized electrolyte in a three-phase mixture has, overall, an undesirably high electronic contribution to the conductivity, the device is incapable of accurately sensing oxygen concentrations below about 10 parts per million. Moreover, the electromotive force developed by such cells decreases substantially with time due to a progressive short-circuit of the cell. At the same time, such tubes are relatively expensive to manufacture.

A further type of oxygen sensor proposed for use in metallurgical melts is the "needle sensor". See, in this regard, Janke, Solid State Ionics, vol. 3, pp. 599-604 (1981). This sensing device is fabricated through an expensive sputtering technique whereby a molybdenum wire is typically coated with sputtered chromium oxide and then overcoated with sputtered stabilized zirconia. It been found that such sensors are incapable of measuring low oxygen concentrations (less than about 20 ppm).

Excellent improvement in the performance and long-term sensing capabilities of electrochemical sensors, especially oxygen sensors, have been developed by two of the inventors of the present invention. These improvements are disclosed in Worrell et al. *New Zirconia-electrolyte Sensors for Measuring Oxygen in Iron and Steel Melts, Proceedings of the Symposium on Chemical Sensors*, D. R. Turner, ed., sponsored by the Electrochemical Society Inc. Vol. 87-9 (1987); and U.S. Pat. Nos. 4,627,892, issued Dec. 9, 1986 and 4,786,374, issued Nov. 22, 1988, each of which is incorporated herein by reference. In accordance with these improvements, zirconia—electrolyte sensors are formed using an isostatic pressing technique to eliminate the then-conventional sintering process and to avoid thermal shock problems associated with prior oxygen and other sensors. In accordance with these developments, oxygen concentrations in melts could be measured over time periods, as long as ten hours.

In the preparation of sensors such as oxygen sensors which employ solid state electrolytes, it is known to be desirable to maximize the ionic conductivity of the electrolyte material and to minimize the electrical conductivity thereof. Sensing electrolytes having substantial electronic conductivity exhibit unstable results at low concentrations of oxygen when the electronic conductivity increases. It is also desired to maximize the intimacy of contact between the electrode material and that of the reference electrode material so as to minimize the equilibration time at the interface between the two materials. Of course, all of this must be obtained while maintaining acceptable physical integrity mechanical strength and thermal shock resistance in the whole of the sensor.

It is also highly desirable to furnish electrochemical sensors which have increased sensing lifetimes, preferably at least on the order of several days. Accordingly, the properties of electrochemical sensors, especially the sensing output, must remain stable for the lifetime of the sensor. While the improvements of U.S. Pat. Nos. 4,627,892 and 4,786,374 are very substantial, ten hours and more in some circumstances, further improvements are still required. Thus, it remains highly desirable to prepare electrochemical sensors, especially oxygen sensors, for use in melts, which are accurate, are stable for extended time periods and which are, at once, not overly costly to manufacture.

The sensors in accordance with the embodiments of the present invention solve the needs which exist for such improved long-term sensors which are capable of manufacture at reasonable cost.

OBJECTS OF THE INVENTION

It is a principal object of this invention to provide electrochemical sensors, especially those for harsh environments, having improved electrochemical and physical properties.

It is another object of this invention to provide processes for the preparation of improved electrochemical sensors.

Another object is to provide improved methods for measuring activity or concentration of an atomic or molecular species, especially under harsh conditions or at high temperatures.

A still further object is to provide electrochemical sensors which are capable of fabrication at reasonable costs while obtaining improved performance and physical properties.

A still further object is to secure the improved processing of metals through a longer-term, more accurate and more sensitive monitoring of the content of metallurgical melts.

Yet another object of the present invention is to provide improvements of electrochemical sensors generally by providing means for improving the physical contact between reference electrode compositions and the electrochemically sensitive species of the sensor.

These and other objects of the invention will become apparent from a review of the instant specification.

SUMMARY OF THE INVENTION

In accordance with this invention, electrochemical sensors for atomic or molecular species are constructed comprising protective sheath means having at least one opening therein. Within the protective sheath means and sealed thereto at the opening is a sensing body. The sealing at the opening is performed in such a manner that a portion of the sensing body is exposed through the opening.

The sensing body comprises a blend formed from a metal oxide and, admixed with the metal oxide, an oxide of an element from Group IIA or IIB of the periodic table of the elements in an amount sufficient to render the blend ionically conductive. The sensing body preferrably comprises a solid solution having a fluorite crystal lattice structure.

The electrochemical sensors of the present invention further comprise reference electrode composition in physical contact with the sensing body.

The sensing body adjacent to the portion which is exposed through the opening in the protective sheath means is relatively thick, having a thickness of at least about 5 mm and preferably from about 6 to about 15 mm.

In accordance with preferred embodiments, the reference electrode composition is contained within a cavity in the sensing body itself. It is preferred that resilient means be provided for urging the reference electrode composition into intimate contact with the sensing body as to improve performance characteristics of the resulting sensors. It is also preferred that lead means be provided for transmitting electrical potential from the sensor as a whole to a measurement apparatus. Oxygen "getting" composition capable of chemically reacting with oxygen is preferably also provided within the protective sheath means.

It is preferred that the sensing body have generally radial symmetry about a longitudinal access to form at least one end wall and a side wall defining a cavity. The end wall is preferably that portion of the sensing body which is adjacent to the opening in the protective sheath means to form the exposed portion of the sensing body. The cavity thus formed is ideally suited for inclusion of the reference electrode composition.

In accordance with other preferred embodiments, the metal oxide is either zirconia, thoria, hafnia or mixtures thereof. The admixed metal oxide preferably comprises scandium, yttrium, calcium or magnesium oxide or mixtures thereof.

Preferred reference electrode composition comprises a mixture of a metal and its oxide especially chromium/chromium oxide or molybdenum/molybdenum oxide.

The sensing body in accordance with the present invention may be porous or substantially non-porous. Thus, certain embodiments of the present invention may benefit from the nonthermal densification procedures taught by U.S. Pat. No. 4,027,892 which has been incorporated herein by reference, however relatively porous structures may also be employed in accordance with certain embodiments.

The invention provides methods for monitoring the concentration of a species in a melt by contacting the melt with an electrochemical sensor in accordance with the present embodiment, by measuring the chemical activity of the sensor a plurality of times and by relating said measurement of electrochemical activity to the concentration of the species in the melt.

In accordance with other preferred embodiments, electrochemical sensors are provided which are particularly sensitive towards oxygen concentration in melts. It is, thus, preferred to provide sensing bodies comprising a zirconia composition. It is preferred that the zirconia sensing body be a blend comprising zirconia admixed with an amount of magnesia, calcia, or yttria sufficient to render the blend ionically conductive. The amount of admixed metal oxide for inclusion in a zirconia sensing body is preferably up to about 30% by weight of the zirconia sensing body as a whole. It is still more preferred that amounts of from 2 to about 15% by weight of the zirconia sensing body be employed. Reference electrode compositions preferred for use with zirconia sensing bodies for the sensing of oxygen concentration in melts include chromium/chromium dioxide and molybdenum/molybdenum dioxide.

Methods for monitoring the concentration of oxygen in a melt are also provided by contacting the melt with an electrochemical sensor for oxygen as described, measuring the chemical activity of the sensor a plurality of times and relating said measurements of chemical activity to the oxygen concentration in the melt.

This invention also provides improvements in electrochemical sensors generally. Electrochemical sensors comprising a sensing body and reference electrode composition may be improved by providing resilient means as part of said sensors which are adapted for urging the reference electrode composition into intimate physical contact with the sensing body. These improvements do not rely upon the particular chemical identity of the sensing body and the reference electrode composition but, rather, are generally applicable to all electrochemical sensing systems.

DETAILED DESCRIPTION OF THE PREFERRED EMBODIMENTS

It has now been found that a totally new approach to the preparation of electrochemical sensors, especially those for use in metallurgical and other melts, can provide such sensors having extremely long lifetimes together with excellent stabilities and sensitivities. Such sensors having excellent thermal shock resistance along with high ionic conductivity, low electronic conductivity and excellent sensitivity can now be prepared which are capable of economical manufacture. It is now possible for the first time to prepare electrochemical sensors, such as oxygen sensors for metallurgical melts, which are stable, sensitive, useful for long periods of time, and able to be manufactured at relatively low cost. It is also now possible to prepare such sensors which can be effectively fused. Unlike prior sensors which have been formulated with the maximum possible density, it is possible to construct sensors in accordance with the present invention which are relatively porous. Additionally, unlike the sensors which are described in U.S. Pat. Nos. 4,627,892 and 4,786,374, which have been incorporated herein by reference, isostatic pressing of the sensing materials is not obligatory.

Electrochemical sensors in accordance with the present invention have protective sheath means covering a sensing body. The present protective sheath means, unlike prior sheath means such as aluminum, cardboard and the like which are meant to be consumed in use, are durable. Preferably, such sheaths are formed of alumina or other metal oxides which are stable in metallurgical melts and the like. The protective sheath means is provided with at least one opening and the sensing body is disposed within the sheath and sealed thereto in such a fashion that a portion of the sensing body is exposed through the opening in the protective sheath. The portion of the sensing body which is adjacent the opening in the protective sheath means and which is referred to as the exposed portion of the sensing body, is relatively thick when compared to the thicknesses of prior sensing bodies of electrochemical sensors. The portion of the sensing body in accordance with the present invention which is adjacent to the exposed portion is at least about 5 mm in thickness and preferably up to about 15 mm in thickness.

The electrochemical sensors in accordance the present invention are largely sheathed or protected form exposure to the metallurgical melts or other harsh conditions for which they are designed by the protective sheath means. The portion of the sensing body which is exposed to the metallurgical melt or other harsh conditions is relatively thick, having a thickness adjacent to the exposed portion of greater than about 5 mm. This combination of factors runs contrary to expectations of persons of ordinary skill in the art but leads to exceptional performance characteristics of the resulting sensors. Thus, contrary to prior expectations, electrochemical response times are not increased in spite of the fact that much of the surface area of the sensing body is not in contact with the metallurgical melt or other material to be sensed by virtue of the fact that it is within the protective sheath means. This is directly contrary to the efforts of prior workers who attempted to maximize the surface area of the sensing body exposed to the material to be sensed in order to improve the response time of the sensors thus designed. The present inventors have found that such maximization of surface area leads to substantial degradation of sensor performance which is contrary to long life in the sensor. It is, accordingly, highly surprising that the relatively small amount of surface area which is exposed to the metallurgical melt or other material to be sensed still permits an excellent response time in the sense was built in accordance with the embodiments of the present invention. The present invention also provides a relatively thick exposed portion of the sensing body of the electrochemical sensors thus formed. Prior workers in the field stringently avoided such large thicknesses in the sensing bodies of their sensors since such thick structures were thought to be relatively sensitive to thermal shock. It has now been discovered, however, that the protection of most of the sensing body by the protective sheath means achieves excellent thermal shock resistance thus permitting the exposed portion of the sensing body to be relatively thick. This thickness is highly beneficial to the performance of the resulting sensors because of the high resistance to electron transport in that portion of the sensing body. The resulting benefit is that the sensors in accordance with the present invention have extremely long life times; much longer than those found by prior workers. Indeed it has been found that the resistance to electronic short circuit of the present sensors are up to 100 times greater than prior commercial sensor.

The sensors which are objects of the present invention are solid state electrochemical sensors for atomic and molecular species. Thus, members of the family of sensing devices which exist in the solid state and which are capable of generating an electromotive force, EMF, upon contacting the atomic or molecular species to be sensed, are objects of this invention. The present improvements were developed especially for use in the extraordinarily harsh conditions which attend metallurgical purification and processing in metallurgical melts. Exemplary of these is the processing of iron and steel. Thus, the sensors and methods in accordance with this invention are particularly suitable to the determination of oxygen and, it is believed, carbon, sulfur and other chemical species in metallurgical melts.

It is believed that the instant sensors and the related methods may also find utility in environments other than metallurgical melts such as high temperature reaction vessels or atmospheres, flue gasses, power boilers, pollution control equipment, and a whole host of oxidative, corrosive, high temperature, and other harsh environments. It is also anticipated that sensing devices in accordance with this invention will also find utility in less harsh environments as well.

For the detection of sulfur or carbon, it is preferred to employ compositions similar to those disclosed in U.S. Pat. No. 4,428,770, incorporated herein by reference. Thus, a carbide or sulfide of an element of group IIA or IIIB of the periodic table is preferably also included.

Sensors in accordance with this invention comprise ionically conductive materials which are sensitive to the species to be detected. In this regard, those of ordinary skill in the art appreciate that electrochemical sensors are desired to have the greatest possible ionic conductivity while, at the same time, having the smallest possible electronic conductivity. Sensing devices having relatively large ionic conductivities coupled with relatively small electronic conductivities are able to demonstrate relatively high reliability and reproducibility in detecting the activity or concentration of the species. It is necessary to select ionically conducting materials which are suitable for the detection of the species to be detected. In most cases, such conducting materials will comprise blends comprising or preferably consisting of solid solutions having fluorite lattice structure.

For detection of oxygen in metallurgical melts, it is preferred to employ metal oxides having a fluorite crystal structure or capable of having solid solutions with such structures such as zirconia, hafnia, thoria, ceria and lanthania. It is preferred to employ materials based upon zirconium dioxide, since that material is known to generate adequate EMF's in metallurgical melts and to be generally suitable as a base material for sensing devices for such employment. Mixtures may also be useful.

It is also generally understood that the metal oxides which are sensitive to the species to be sensed, i.e., which generate an EMF when in contact with such species, are seldom able to be fabricated into suitable electrochemical sensors without modification into a blend to improve the ionic conductivity. Accordingly, an oxide from group IIA or IIIB of the periodic table is preferably blended with the metal oxide through admixture in proportions sufficient to render the resulting blend ionically conductive to a degree sufficient for sensing. Such oxides for admixture may comprise calcium, magnesium, strontium, barium, scandium, yttrium and lanthanum oxides and mixtures thereof. It is greatly preferred that the admixed oxide be included in the blends with metal oxide in proportions which permit the blends to comprise solid solutions which retain fluorite crystal structures. In this regard, proportions which are consistent with this goal may be determined in accordance with the procedures of "Oxide Solid Electrolytes", Worrell, Topics in Applied Physici, Vol. 21, p. 143 et seq., Springer (1977), which is incorporated herein by reference. In the case of zirconium oxide sensors designed for use in metallurgical melts for the detection of oxygen, it is preferred to employ metal oxides such as calcium, magnesium, yttrium, or scandium oxide for this purpose. Yttria and calcium oxide are most preferred. Additional aliovalent materials may be useful for modification of the preferred zirconium oxide materials. Those of ordinary skill in the art will understand that routine experimentation may be necessary in order to identify preferred aliovalent compositions for particular sensing systems in accordance with these embodiments.

Admixed oxide is blended with the metal oxides in an amount sufficient to improve the ionic conductivity and, preferably, also the physical stability of the resulting sensors formed therefrom. Thus, the metal oxide and admixed oxide are blended to form a blend which is useful in the subsequent formation of the electrochemical sensors of the invention. While admixed oxide is included in an amount sufficient to improve ionic conductivity of the resulting blend, in general, amounts of admixed oxide up to about 30% and preferably between about 2 and 25% and more preferably between about 2 to 15% by weight are preferred for most zirconium oxide systems.

Electrolyte blends for formation of sensing bodies can be preferably prepared from yttria-stabilized, calcia-stabilized, and magnesia-stabilized zirconia powders. Thus, 99.9% pure zirconia powder is admixed with approximately 12 mole percent (11 wt. %) of $Y_2O_3$, approximately 2-3 wt. % or about 5.9 to 8.6 mol. % $MgO_2$, or approximately 15 mole percent (7.4 wt. %) caO for use as electrolyte materials. Other compositions such as about 6-15 mole percent (5.5 to 14 wt. %) yttria-zirconia and about 7-16 mole percent (3.3 to 8 wt. %) calcia-zirconia are also suitable for such electrolytes. The average particle sizes for the foregoing materials are maintained within the range of about 0.1 to about 5 microns and preferably within the range of 0.3 to about 1.5 microns. The zirconia-yttria, zirconia-calcia, or zirconia-magnesia blend is than pre-pressed in a rubber mold at 50,000 psi using an isostatic press. The pre-pressed block is then crushed to −50 mesh powder (less than about 300 microns) and this coarse powder used to prepare sensing bodies. Partially-stabilized zirconia electrolytes can be similarly prepared through admixture of magnesia, such as about 2-3 wt. %, with zirconia.

The foregoing blend is preferably provided in particle sizes and forms which are maximally suited for the practice of this invention. Thus, it is preferred to employ aggregates of smaller particles of blend yielding average aggregate sizes between about 100 and 500 microns in the blend. For zirconium oxide oxygen sensing systems, it is preferred to employ aggregate sizes between about 150 and about 425 microns. Other systems may beneficially employ differing particle size ranges, however.

The foregoing aggregate sizes are preferably achieved by isostatic compression of the blend. Thus, the blend is preferably isostatically compressed at a pressure in excess of about 30,000 psi to form a compressed shape which is subsequently comminuted in a conventional crushing process to yield the desired aggregate sizes. For zirconium oxide oxygen sensors, it is preferred to undertake this pressing using pressure of about 50,000 psi. The blends are preferably sintered prior to aggregation through isostatic compression. Such materials are commercially available preblended and sintered.

In accordance with one preferred embodiment of the present, the crushed aggregate is compressed into a shaped body which forms the sensing body in accordance with the invention. This formation may be conveniently performed in accordance with any of the methods known to persons of ordinary skill in the art. Thus, the body thus formed may be sintered or not depending upon the preferences of such persons. It is not necessary that the sensing body be especially dense or non-porous since porous structures have been found to be useful in the practice of the present invention in view of the protective nature of the protective means provided herein.

In accordance with other preferred embodiments, however, a second, isostatic compression step is performed. Thus, the blend is formed into a sensing body under isostatic pressure preferably in excess of about 70,000 psi. For zirconium oxide oxygen sensors, isostatic compression to form the sensing body preferably takes place at pressures in excess of about 75,000 and even more preferably in excess of about 80,000 psi. Compression is maintained for a period of time sufficient to form the sensing body and to cause the same substantially to coalesce. A few minutes is generally sufficient for this purpose.

Isostatic compression can be achieved in a number of ways. Generally, an amount of the blend is encapsulated by a physically deformable matrix, such as a matrix of rubber, and caused to be subjected to pressure. By virtue or the deformability of the deformable composition or rubber, substantially identical pressures are exerted on all portions of the compressed blend. The blend may be isostatically compressed into any number of shapes to form the sensing body of the invention. While it is convenient to provide generally cylindrical shapes freeform, ovoid, rectilinear, and other shapes may also be employed.

The resulting shaped body, when fitted with appropriate sources of reference potential and EMF measuring means, is capable of detecting the presence of species such as oxygen in metallurgical melts. As will be explained more fully hereinafter, the sensing body is preferably elaborated into a more complex device in order t facilitate sensing procedures.

The sensing bodies are provided with a source of reference potential in physical contact therewith. As will be appreciated by those of ordinary skill in the art, numerous sources of reference potential for solid state electrochemical sensing devices are known. Such persons will have no difficulty in identifying suitable materials for use as a source of reference potential. While it is also possible to use gaseous or liquid means for the attainment of reference potential, solid state sources are much preferred.

It is generally preferred to employ compositions comprising mixtures of a metal and a metal oxide for use as a source of reference potential in conjunction with zirconium oxide metallurgical oxygen sensors. Numerous metal-metal oxide combinations may be employed for this purpose including preferred blends based upon chromium and molybdenum. For zirconium oxide based metallurgical oxygen sensors, reference electrodes comprising chromium-chromium oxide, or molybdenum oxide are preferred. It is also desirable to pre-sinter the reference composition to reduce its volume shrinking.

Preferred reference electrode sources are prepared from blends of molybdenum and molybdenum oxide or chromium and chromium oxide having purities of about 99.9%. If molybdenum and molybdenum oxide are used, their particle sizes are approximately −325 mesh. If chromium and chromium oxide are used, they are conveniently present in particle sizes of about 2 microns and 5 microns respectively. The foregoing materials are available from the Alfa Company.

Another promising reference material is a chromium/iron alloy in a two-phase region. Such alloys have fixed electrochemical potential and are conceived to be highly useful.

In accordance with preferred embodiments of the present invention, the reference electrode composition is included within the protective sheath means of the electrochemical sensors. It has been found to be convenient to prepare the sensing body in such a fashion that it includes a cavity within it. Reference electrode material can be incorporated within that cavity and sealed therein to effect intimate physical contact between the reference electrode composition and the sensing body. Persons of ordinary skill in the art appreciate that such intimate physical contact is highly desirable.

Other preferred components of sensors in accordance with the invention are described with reference to the drawings.

Figure 1:
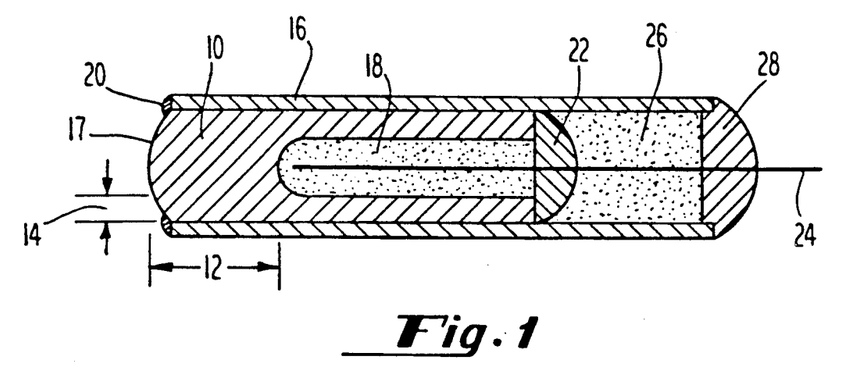
FIG. 1 depicts and electrochemical sensor in accordance with certain embodiments of the instant invention.

FIG. 1 depicts a cross-section an electrochemical sensor in accordance with a preferred embodiment of the present invention. Sensing body, 10 is disposed within and preferably, generally in contact with a protective sheath means, 16 having at least one opening therein. The sensing body is sealed with sealant 20 in such a fashion that a portion of the sensing body is exposed through the opening in the protective sheath. The protective sheath means is preferably a material which is impervious to conditions under which measurement is to be obtained. Thus, for use in metallurgical melts and the like, alumina, porcelain or other thermomechanically strong structures are preferred. The sealant material is selected so as to be stable under the conditions to be experienced during measurement, such as metallurgical melts and the like. These sealant compositions must not exude water or oxygen and must a co-efficient of thermal expansion which is suitable to effect sealing between the protective sheath means and the sensing body. Various cements are suitable for such use including AMCO high temperature alumina cement.

Electrical chemical sensors of this embodiment are also provided with reference electrode material 18 in physical contact with the sensing body 10. It is preferred that the reference electrode material be disposed within a cavity within the sensing body as shown. It is preferred that the sensing body 10 have radial symmetry about a longitudinal access. Thus, such geometry will form an end wall having a thickness, 12 and a side wall having a generally lesser thickness, 14 and preferably forms a cavity for inclusion of reference electrode material. The portion of the sensing body 10 which is exposed, exposed portion 17, is arranged such that the portion of the sensing body adjacent to the exposed portion has a thickness in the figure, end wall thickness 12 of at least about 5 mm and preferably between 6 and 10 mm. While the side wall thickness is less critical, it is preferred that the side wall thickness be less than the thickness of the end wall, on the order of 0.5 to 2 mm. It is preferred that the reference electrode composition be sealed within a cavity within the sensing body. This sealing is accomplished with sealant 22 which may be either the same or different from sealant 20 but which, nonetheless, must be stable under the conditions for which sensing is desired. In order to avoid the presence of oxygen within the sensors of the present invention, it is preferred that an oxygen getter 26 be provided interior to the protective sheath means. A preferred getter is molybdenum powder. The entirety of the foregoing materials are then sealed with sealant 28 which, again, may be either the same or different from sealants 20 and 22.

Lead means 24 is also provided to serve as an electrical conduit for the measurement of electrical potential generated by the electrochemical reactions experienced by the sensors of the invention. The lead means may be any suitable composition but is preferably molybdenum metal. The lead is run into the reference electrode composition as shown and is maintained in intimate contact therewith. In accordance with preferred embodiments, the lead means may be crimped or shaped in order to improve such physical intimacy.

Figure 2:
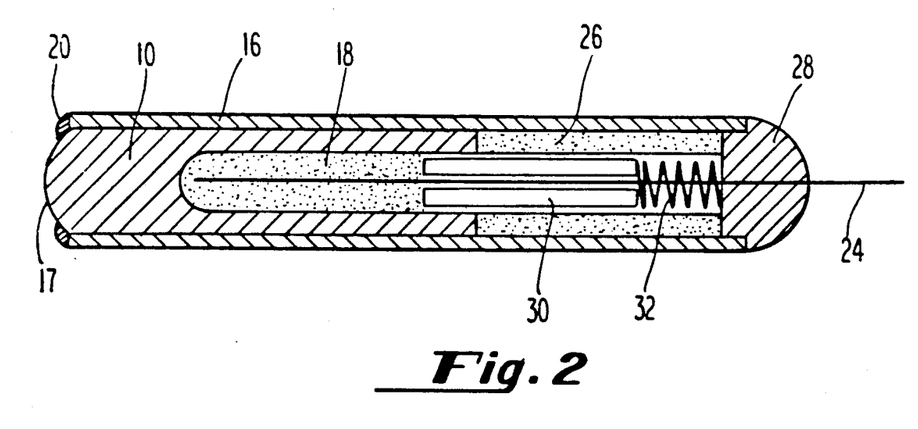
FIG. 2 depicts another electrochemical sensor in accordance with preferred embodiments of the present invention, including resilient means for urging the reference electrode composition into intimate physical contact with an electrochemical sensing body.

FIG. 2 is another embodiment of the present invention illustrating certain preferred adaptations. This embodiment depicts slightly different arrangements of sensing body, 10, reference electrode material 18 and oxygen getter, 26 disposed within protective sheath means 16. The sensing body 10 is still sealed to sheath 16 with sealant 20 to form exposed portion 17 at an opening in the protective sheath means. This embodiment also provides means for improving the desired intimate physical contact between reference electrode material and the sensing body. Thus, a spring 32 or other source of resilient force is provided to expert a force upon a compression rod 30 to cause the same to push upon the reference electrode material 18 causing it to have intimate physical contact with the sensing body 10. Taken together, the spring or other source of resilient effort combined with the optional compression rod or other device for transmitting this effort to the reference electrode composition is denominated resilient means. Once again, sealant composition 28 and lead means 24 are provided to complete the electrochemical sensor.

Not shown in the foregoing figures are the conventional means for representing the electrochemical potential which is established upon the contacting of sensors in accordance with the invention with the materials to be sensed. Thus, meter, graph, computer, or other means for visualizing, displaying or determining this electrochemical potential are conventional as will be appreciated by persons of ordinary skill in the art.

It is also preferred to provide a thermocouple, preferably one comprising a platinum/6% rhodium vs. platinum/30% rhodium chemical combination. Such thermocouples are conventionally available such a from the Englehard Co. of New Jersey.

In practice, the material to be sensed, usually a metallurgical melt, is contacted with a sensor in accordance with the invention and the electrochemical potential of the sensor measured, preferably over time. The electrochemical activity is determined by the potential expressed from the cell through the lead means either to a meter, computer, or analyzing circuit. By relating the electrochemical potential thus determined to electrochemical potential which is experienced for a series of standards, the absolute value of the oxygen or other species concentration within the material to be sensed can be determined.

In accordance with a preferred embodiment, the oxygen concentration of a metallurgical melt, especially steel, is determined by contacting that melt with the sensor in accordance with the invention. It is preferred that a plurality of measurements be made over time for the determination of the oxygen concentration.

In accordance with another aspect of the invention, electrochemical sensors in general are improved by providing resilient means for urging reference electrode composition into improved physical contact with a sensing body. Thus, any electrochemical sensor comprising a sensing body means and a reference electrode composition may be so improved by providing resilient needs for urging reference electrode composition into intimate physical contact with the sensing body. This is not limited to electrochemical sensors for use in metallurgical melts but may apply generally to the field of electrochemical sensors.

Certain preferred embodiments will be discussed in accordance with the following examples. These examples are intended to be illustrative only and are not to be construed as limiting.

EXAMPLE 1

An oxygen sensor in accordance with a preferred embodiment of the present invention was prepared from partially-stabilized zirconia. Zirconia powder (99.9% pure) was mixed with 2.8 wt% of magnesium dioxide powder. The blend comprises particle sizes of between about 0.2 to 0.8 microns. The blend is pressed at a pressure of about 50,000 psi and crushed to −50 mesh powder (less than about 300 microns). A shaped sensing body having the form of a test tube with a thick end was formed by an injection molding. The sensing body had a side wall thickness of about 0.5 mm and an end wall thickness of about 10 mm. Its overall diameter was 6 mm and the length was 35 mm. It was formed with a cavity generally as shown in FIG. 1. The cavity dimensions were diameter 5 mm and length 25 mm.

The sensing body thus formed was provided with a protective sheath which was a sintered alumina tube made by slurry casting. The sheath had an end opening generally as shown in FIG. 1. The sheath was sized to fit snugly about the sensing body, extending beyond its cavity-bearing end. The wall thickness of the sheath was about 1 mm and its end opening had an inner diameter of 6.5 mm.

The reference electrode composition of molybdenum and molybdenum oxide (−325 mesh) blended from materials conveniently obtained from the Alfa company, along with a crinkled molybdenum lead were pressed tightly into the cavities of similar sensing bodies and sealed into place with high temperature alumina cement (AMCO). The sensing body containing the reference electrode composition was then sealed to the protective alumina sheath about the opening in the sheath with more of the high temperature alumina cement.

Molybdenum powder for oxygen getting, was then pressed into the space remaining within the protective sheath and the sheath sealed about the molybdenum lead. The resulting sensors were highly suitable for determining the oxygen concentration in metallurgical melts, especially molten iron.

EXAMPLE 2

A sensor in accordance with Example 1 was fabricated except that the reference electrode composition was chromium/chromium oxide blended powder, 2-5 microns, prepared from components obtained from the Alfa company.

The sensors prepared in Examples 1 and 2 were compared with commercially-available oxygen sensors designed for use in molten metals. Tube type sensors, from the Electro Nite company were used for this comparison. The tube type sensor was representative of normal commercial sensors having no protective head. These commercial sensors have useful lifetimes in molten iron of about 20 to 45 seconds.

The sensors of Examples 1 and 2 were compared to the foregoing commercial sensors in metal melts at oxygen concentrations of about 2 to about 50 ppm.

Pure iron was used for testing. The metal was put into an alumina crucible about 30 millimeters in diameter and 60 millimeters high. The iron was melted in a purified argon atmosphere. At a temperature of about 1550° C., the oxygen sensor was inserted into the molten melt for testing. The electromotive force generated by the interaction of the sensor with the melt was measured by a Keithley 177 microvolt DMN meter interfaced with a data collection computer. For long term oxygen sensing tests, the electromotive force was read every minute. For tests of expendable oxygen sensors the electromotive force was read continuously. When employing a chromium-chromium oxide reference electrode, the reference electrode lead was connected to the negative pole of the volt meter. The reference electrode lead was connected to the positive pole of the volt meter for oxygen sensors employing molybdenum-molybdenum oxide reference electrodes.

Figure 3:
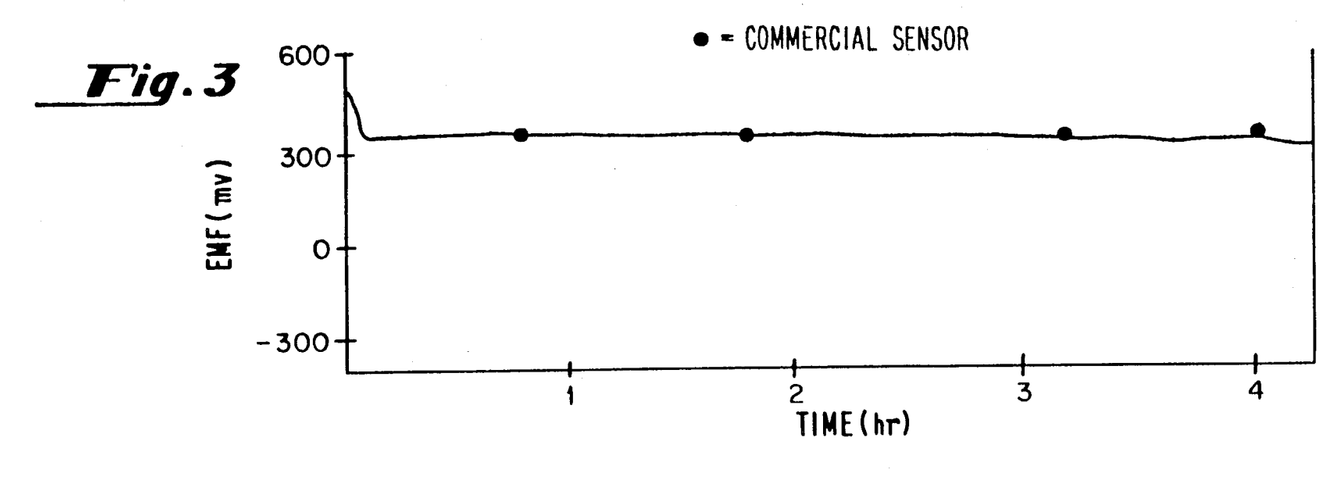
FIGS. 3 and 4 depict the long term stability of preferred sensors of the invention.
Figure 4:
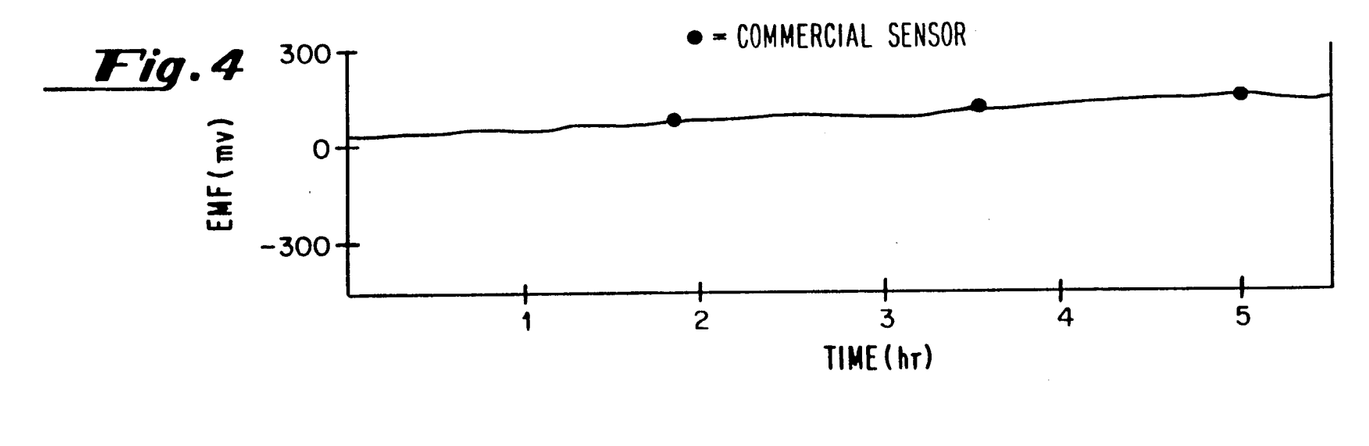

FIGS. 3 and 4 depict the long-term stability of the sensor of Example 1 and Example 2 respectively. The data points shown for the short term commercial sensors convey the excellent agreement between the sensors of this invention and the short term sensors used commercially.

EXAMPLE 4

It is expected that even better performance will be obtained through use of fully stabilized zirconia in place of the partially stabilized zirconia used in Examples 1 and 2. Thus, similar sensors may be prepared employing zirconia admixed with either 3 to 8 wt. % calcia or 4 to 15 wt. % yttria. Even longer term stability is expected with such sensors.

What is claimed is:

1. An electrochemical sensor for determining the concentration of oxygen in a melt, comprising:
   A. protective sheath means having at least one opening therein;
   B. a zirconia sensing body having predetermined length and width and an end wall having predetermined thickness, said sensing body being:
      within said protective sheath means and in contact therewith along substantially the entire length of the sensing body; and
      sealed to said protective sheath means at said opening to expose a portion of the zirconia sensing body; and
   c. reference electrode composition in contact with said zirconia sensing body;
   the thickness of the end wall adjacent to the exposed portion being greater than the width of the sensing body and being at least about 5 mm.

2. The electrochemical sensor of claim 1 wherein the thickness of the zirconia sensing body end wall adjacent to the exposed portion is from about 6 mm to about 10 mm.

3. The electrochemical sensor of claim 1 wherein the reference electrode composition is contained within a cavity in the zirconia sensing body.

4. The electrochemical sensor of claim 1 further comprising lead means in electrical contact with said reference electrode composition.

5. The electrochemical sensor of claim 1 further comprising oxygen getting composition within the protective sheath.

6. The electrochemical sensor of claim 1 further comprising resilient means for urging the reference electrode composition into intimate contact with the zirconia sensing body.

7. The electrochemical sensor of claim 1 wherein the zirconia sensing body has generally radial symmetry about a longitudinal axis and comprises wall defining a cavity.

8. The electrochemical sensor of claim 7 wherein the reference electrode composition is contained within said cavity.

9. The electrochemical sensor of claim 1 wherein said zirconia sensing body is a blend comprising zirconia admixed with an amount of scandia, magnesia, calcia or yttria sufficient to render the blend ionically conductive.

10. The electrochemical sensor of claim 9 wherein said amount is up to about 30% by weight of the zirconia sensing body.

11. The electrochemical sensor of claim 9 wherein said amount is from about 2 to about 15 percent by weight of the zirconia sensing body.

12. The electrochemical sensor of claim 1 wherein said reference electrode composition is chromium/chromium dioxide.

13. The electrochemical sensor of claim 1 wherein said reference electrode composition is molybdenum/molybdenum dioxide.

14. The electrochemical sensor of claim 1 wherein the reference electrode composition comprises a chromium/iron alloy in a two phase region which has a fixed chemical potential.

15. The electrochemical sensor of claim 1 wherein said protective sheath means comprises alumina.

16. The electrochemical sensor of claim 1 wherein the zirconia sensing body is isostatically formed and is substantially non-porous.

17. A method for monitoring the concentration of oxygen in a melt comprising:
  A. contacting said melt with an electrochemical sensor comprising:
    1. protective sheath means having at least one opening therein;
    2. a zirconia sensing body having predetermined length and width and an end wall having predetermined thickness, said sensing body being:
       within said protective sheath means and in contact therewith along substantially the entire length of the sensing body, and
       sealed to said sheath means at said opening to expose a portion of the zirconia sensing body; and
    3. reference electrode composition in contact with said zirconia sensing body;
    the thickness of the end wall adjacent to the exposed portion being greater than the width of the sensing body and being at least about 5 mm;
  B. measuring the electrochemical potential of said sensor a plurality of times; and
  C. relating said measurements of electrochemical potential to the oxygen concentration in the melt.

18. The method of claim 17 wherein said melt is at a temperature of at least about 1400° C.

19. The method of claim 18 wherein said melt is a ferrous melt.

* * * * *